United States Patent [19]

Ohta

[11] Patent Number: 4,529,678
[45] Date of Patent: Jul. 16, 1985

[54] ELECTROPHOTOGRAPHIC PHOTOCONDUCTOR COMPRISING A DITHIOL DERIVATIVE

[75] Inventor: Masafumi Ohta, Susono, Japan

[73] Assignee: Ricoh Company, Ltd., Tokyo, Japan

[21] Appl. No.: 533,842

[22] Filed: Sep. 20, 1983

[30] Foreign Application Priority Data

Oct. 25, 1982 [JP] Japan ............................. 57-187220

[51] Int. Cl.³ .............................................. G03G 5/14
[52] U.S. Cl. ........................................ 430/58; 430/59; 430/75
[58] Field of Search .......................... 430/75, 59, 58

[56]  References Cited

U.S. PATENT DOCUMENTS 3,871,882  3/1975  Wiedemann ................ 430/58 X
4,346,159  8/1982  Sadamatsu et al. ......... 430/66 X
4,363,829 12/1982  Seshimoto et al. ......... 430/58 X
4,439,505  3/1984  Perlstein et al. ............ 430/62 X Primary Examiner—John D. Welsh
Attorney, Agent, or Firm—Flynn, Thiel, Boutell & Tanis

[57]  ABSTRACT

An electrophotographic photoconductor is disclosed, which comprises an electroconductive support material and a photosensitive layer comprising at least one 1,3-dithiol derivative of the formula

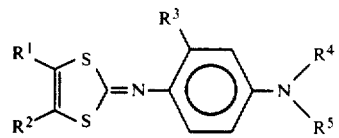

wherein $R^1$ and $R^2$ independently represent hydrogen, a substituted or unsubstituted phenyl group, or $R^1$ and $R^2$ in combination can form a ring; $R^3$ represents hydrogen or an alkyl group; and $R^4$ and $R^5$ independently represent an alkyl group, a substituted or unsubstituted aralkyl group, or a substituted or unsubstituted aryl group.

10 Claims, 3 Drawing Figures

ELECTROPHOTOGRAPHIC PHOTOCONDUCTOR COMPRISING A DITHIOL DERIVATIVE

BACKGROUND OF THE INVENTION

The present invention relates to an electrophotographic photoconductor, and more particularly to an electrophotographic photoconductor comprising a photosensitive layer containing a 1,3-dithiol derivative overlayed on an electroconductive support material.

Conventionally, a variety of inorganic and organic electrophotographic photoconductors are known. As inorganic photoconductors for use in electrophotography, there are known types, in which the photoconductive material is, for instance, selenium, cadmium sulfide, and zinc oxide. In an electrophotographic process, a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic photoconductors have many advantages over other conventional electrophotographic photoconductors, at the same time they have several shortcomings from the viewpoint of practical use.

For instance, a selenium photoconductor, which is widely used at present, has the shortcoming that its production is difficult and, accordingly, its production cost is high. Further, it is difficult to work it into the form of a belt due to its poor flexibility, and it is so vulnerable to heat and mechanical shocks that it must be handled with the utmost care.

Cadmium sulfide photoconductors and zinc oxide photoconductors are prepared by dispersing cadmium sulfide or zinc oxide in a binder resin. They can be produced inexpensively compared with selenium photoconductors and are also used commonly in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have the such shortcomings of the inorganic electrophotographic photoconductors, have been proposed, and some of them are in fact employed for practical use. Representative examples of such organic electrophotographic photoconductors are an electrophotographic photoconductor comprising poly-N-vinylcarbazole and 2,4,7-trinitro-fluorene-9-one (U.S. Pat. No. 3,484,237); a photoconductor in which poly-N-vinylcarbazole is sensitized by a pyrylium salt type coloring material (Japanese Patent Publication No. 48-25658); a photoconductor containing as the main component an organic pigment (Japanese Laid-Open Patent Application No. 47-37543); and a photoconductor containing as the main component an eutectic crystaline complex (Japanese Laid-Open Patent Application No. 47-10735).

Although the above-mentioned organic electrophotographic photoconductors have many advantages over other conventional electrophotographic photoconductors, they still have several shortcomings from the viewpoint of practical use, in particular, for use in high speed copying machines, in terms of cost, production, durability and electrophotographic sensitivity.

SUMMARY OF THE INVENTION

It is therefore an object of the present invention to provide an electrophotographic photoconductor or element comprising a photoconductive layer containing a 1,3-dithiol derivative and an electroconductive support material for supporting the photoconductive layer thereon, with high photosensitivity and uniform spectral absorption in the visible region, which does not give rise to difficulties in producing the electrophotographic photoconductor, and which is comparatively inexpensive and excellent in durability.

The 1,3-dithiol derivative employed in the present invention is represented by the following general formula:

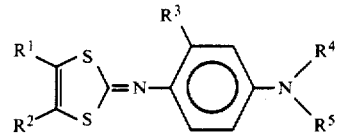

wherein $R^1$ and $R^2$ independently represent hydrogen, a substituted or unsubstituted phenyl group, or $R^1$ and $R^2$ in combination can form a ring; $R^3$ represents hydrogen or an alkyl group; and $R^4$ and $R^5$ independently represent an alkyl group, a substituted or unsubstituted aralkyl group, or a substituted or unsubstituted aryl group.

DETAILED DESCRIPTION OF THE PREFERRED EMBODIMENTS

The electrophotographic photoconductor according to the present invention is characterized by having a photosensitive layer which comprises at least one 1,3-dithiol derivative of the following formula (I):

described, for instance, in Journal of Synthetic Organic Chemistry, Japan, Vo. 39, page 192 (1981).

Specific examples of 1,3-dithiol derivatives of the above formula are shown in Table 1.

TABLE 1

| Compound No. | $R^1$ | $R^2$ | $R^3$ | $R^4$ | $R^5$ |
|---|---|---|---|---|---|
| 1 | -phenyl | H | H | $-CH_3$ | $-CH_3$ |
| 2 | -phenyl | H | H | $-C_2H_5$ | $-C_2H_5$ |
| 3 | -phenyl | H | $-CH_3$ | $-C_2H_5$ | $-C_2H_5$ |
| 4 | -phenyl | H | H | $-CH_2-$phenyl | $-CH_2-$phenyl |
| 5 | -phenyl | H | H | -phenyl | -phenyl |
| 6 | -phenyl | H | H | $-CH_2-$phenyl$-CH_3$ | $-CH_2-$phenyl$-CH_3$ |
| 7 | -phenyl | H | H | $-CH_2-$phenyl$-OCH_3$ | $-CH_2-$phenyl$-OCH_3$ |
| 8 | -phenyl-$CH_3$ | H | $-CH_3$ | $-C_2H_5$ | $-C_2H_5$ |
| 9 | -phenyl-$OCH_3$ | H | $-CH_3$ | $-C_2H_5$ | $-C_2H_5$ |
| 10 | -phenyl-$OCH_3$ | H | H | -phenyl | -phenyl |

wherein $R^1$ and $R^2$ independently represent hydrogen, a substituted or unsubstituted phenyl group, or $R^1$ and $R^2$ in combination can form a ring; $R^3$ represents hydrogen or an alkyl group; and $R^4$ and $R^5$ independently represent an alkyl group, a substituted or unsubstituted aralkyl group, or a substituted or unsubstituted aryl group.

Referring to the accompanying drawings, embodiments of an electrophotographic photoconductor according to the present invention will now be explained.

Figure 1:
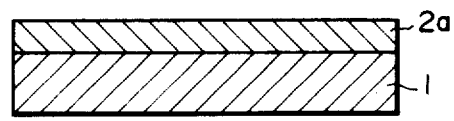
FIG. 1 is an enlarged schematic cross-sectional view of an embodiment of an electrophotographic photoconductor according to the present invention.
Figure 2:
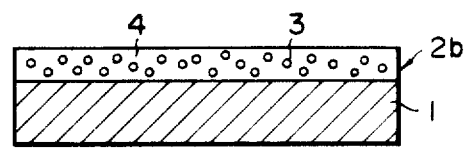
FIG. 2 is an enlarged schematic cross-sectional view of another embodiment of an electrophotographic photoconductor according to the present invention.
Figure 3:
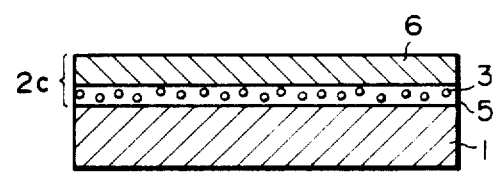
FIG. 3 is an enlarged schematic cross-sectional view of a further embodiment of an electrophotographic photoconductor according to the present invention.

In FIGS. 1 to 3, reference numeral 1 indicates an electroconductive support material; reference numerals 2a, 2b and 2c each indicate a photosensitive layer; reference numeral 3, a charge generating material; reference numeral 4, a charge transporting medium; reference numeral 5, a charge generating layer; and reference numeral 6, a charge transporting layer.

The 1,3-dithiol derivatives of the formula (I) for use in the present invention can be prepared by a procedure In the photoconductors according to the present invention, at least one 1,3-dithiol derivative of the formula (I) is contained in the photosensitive layers 2a, 2b and 2c. The 1,3-dithiol derivatives can be employed in different ways, for example, as shown in FIG. 1, FIG. 2 and FIG. 3.

In the photoconductor shown in FIG. 1, a photosensitive layer 2a is formed on an electroconductive support material 1, which photosensitive layer 2a comprises a 1,3-dithiol derivative, a sensitizer dye and a binder agent. In this photoconductor, the 1,3-dithiol derivative works as a photoconductor material, through which generation and transportation of charge carriers which are necessary for the light decay of the photoconductor are performed. However, the 1,3-dithiol derivative itself scarcely absorbs light in the visible light range and, therefore, it is necessary to add a sensitizer dye which absorbs light in the visible light range in order to form latent electrostatic images by use of visible light.

Referring to FIG. 2, there is shown an enlarged cross-sectional view of another embodiment of an electrophotographic photoconductor according to the present invention. In the figure, reference numeral 1 indicates an electroconductive support material. On the electroconductive support material 1, there is formed a photosensitive layer 2b comprising a charge generating material 3 dispersed in a charge transporting medium 4 comprising a 1,3-dithiol derivative and a binder agent. In this embodiment, the 1,3-dithiol derivative works as a charge transporting material; and the 1,3-dithiol derivative and the binder agent in combination constitute the charge transporting medium 4. The charge generating material 3, which is, for example, an inorganic or organic pigment, generates charge carriers. The charge transporting medium 4 serves to accept the charge carriers generated by the charge generating material 3 and to transport those charge carriers.

In this electrophotographic photoconductor, it is basically necessary that the light-absorption wavelength regions of the charge generating material 3 and the 1,3-dithiol derivative not overlap in the visible light range. This is because, in order that the charge generating material 3 produce charge carriers efficiently, it is necessary that light pass through the charge transporting medium 4 and reach the surface of the charge generating material 3. Since the 1,3-dithiol derivatives of the above described general formula do not substantially absorb light in the visible range, they can work effectively as charge transporting materials in combination with the charge generating material 3 which absorbs the light in the visible region and generates charge carriers.

Referring to FIG. 3, there is shown an enlarged cross-sectional view of a further embodiment of an electrophotographic photoconductor according to the present invention. In the figure, there is formed on the electroconductive support material 1 a two-layered photosensitive layer 2c comprising a charge generating layer 5 consisting essentially of the charge generating material 3, and a charge transporting layer 6 containing a 1,3-dithiol derivative of the previously described formula.

In this photoconductor, light which has passed through the charge transporting layer 6 reaches the charge generating layer 5, and charge carriers are generated within the charge generating layer 5. The charge carriers which are necessary for the light decay for latent electrostatic image formation are generated by the charge generating material 3 and are accepted and transported by the charge transporting layer 6. In the charge transporting layer 6, the 1,3-dithiol derivative mainly works for transporting charge carriers. The generation and transportation of the charge carriers are performed by the same mechanism as that in the photoconductor shown in FIG. 2.

When an electrophotographic photoconductor according to the present invention as shown in FIG. 1 is prepared, at least one 1,3-dithiol derivative of the previously described formula is dispersed in a binder resin solution, and a sensitizer dye is then added to the mixture, and the thus prepared photosensitive liquid is coated on an electroconductive support material 1 and dried, so that a photosensitive layer 2a is formed on the electroconductive support material 1.

It is preferable that the thickness of the photosensitive layer 2a be in the range of 3 μm to 50 μm, more preferably in the range of 5 μm to 20 μm. It is preferable that the amount of the 1,3-ithiol derivative contained in the photosensitive layer 2a be in the range of 30 wt. % to 70 wt. % of the total weight of the photosensitive layer 2a, more preferably about 50 wt. % of the total weight of the photosensitive layer 2a. Further, it is preferable that the amount of the sensitizer dye contained in the photosensitive layer 2a be in the range of 0.1 wt. % to 5 wt. % of the total weight of the photosensitive layer 2a, more preferably in the range of 0.5 wt. % to 3 wt. %, of the total weight of the photosensitive layer 2a.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes, such as Methylene Blue; cyanin dyes, such as cyanin; and pyrylium dyes, such as 2,6-diphenyl-4-(N,N-dimethylaminophenyl) thiapyrylium perchlorate and benzopyrylium salt (Japanese Patent Publication 48-25658). These sensitizer dyes can be used alone or in combination.

An electrophotographic photoconductor according to the present invention as shown in FIG. 2 can be prepared, for example, as follows. A charge generating material in the form of small particles is dispersed in a solution of one or more 1,3-dithiol derivatives and a binder agent. The thus prepared dispersion is coated on the electroconductive support material 1 and is then dried, whereby a photosensitive layer 2b is formed on the electroconductive support material 1.

It is preferable that the thickness of the photosensitive layer 2b be in the range of 3 μm to 50 μm, more preferably in the range of 5 μm to 20 μm. It is preferable that the amount of the 1,3-dithiol derivative contained in the photosensitive layer 2b be in the range of 10 wt. % to 95 wt. %, more preferably in the range of 30 wt. % to 90 wt. % of the total weight of the photosensitive layer 2b. Further, it is preferable that the amount of the charge generating material 3 contained in the photosensitive layer 2b be in the range of 0.1 wt. % to 50 wt. %, more preferably in the range of 1 wt. % to 20 wt. %, of the total weight of the photosensitive layer 2b.

As the charge generating material 3, the following can be employed in the present invention: Inorganic pigments, such as selenium, a selenium-tellurium alloy, cadmium sulfide, a cadminum sulfide - selenium alloy, and α-silicon; and organic pigments, for example, C.I. Pigment Blue 25 (C.I. 21180), C.I. Pigment Red 41 (C.I. 21200), C.I. Acid Red 52 (C.I. 45100), and C.I. Basic Red 3 (C.I. 45210); azo pigments having a carbazole skeleton (Japanese Laid-Open Patent Application 53-95033), azo pigments having a distyrylbenzene skeleton (Japanese Laid-Open Patent Application 53-133445), azo pigments having a triphenylamine skeleton (Japanese Laid-Open Patent Application 53-132347), azo pigments having a dibenzothiophene skeleton (Japanese Laid-Open Patent Application 54-21728), azo pigments having an oxazole skeleton (Japanese Laid-Open Patent Application 54-12742), azo pigments having a fluorenone skeleton (Japanese Laid-Open Patent Application 54-22834), azo pigments having a bisstilbene skeleton (Japanese Laid-Open Patent Application 54-17733), azo pigments having a distyryl oxadiazole skeleton (Japanese Laid-Open Patent Application 54-2129), azo pigments having a distyryl carbazole skeleton (Japanese Laid-Open Patent Application 54-14967); phthalocyanine-type pigments such as C.I. Pigment Blue 16 (C.I. 74100); Indigo-type pigments such as C.I. Vat Brown 5 (C.I. 73410) and C.I. Vat Dye (C.I. 73030); and perylene-type pigments, such as Algo Scarlet B (made by Bayer Co., Ltd.) and Indanthrene Scarlet R (made by Bayer Co., Ltd.). These charge generating materials can be used alone or in combination.

Of the above-mentioned charge generating materials, the following three types of the azo pigments are particularly effective for use in the present invention:

(1) Azo pigments having a distyrylbenzene skeleton (Japanese Laid-Open Patent Application 53-133445)

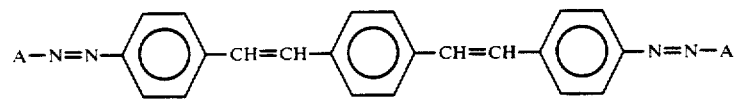

wherein A is selected from the group consisting of

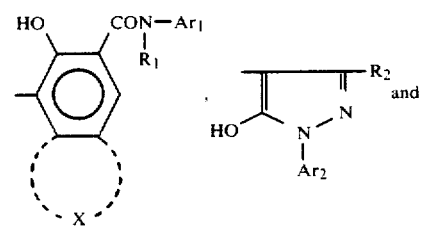

and

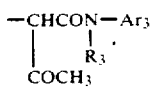

(wherein X is selected from the group consisting of aromatic rings such as a benzene ring, a naphthalene ring, heterocyclic rings such as an indole ring, a carbazole ring, a benzofuran ring, and substituted aromatic rings and substituted heterocyclic rings; $Ar_1$ is selected from the group consisting of aromatic rings such as a benzene ring, a naphthalene ring, heterocyclic rings such as a dibenzofuran, and substituted aromatic rings and substituted heterocyclic rings, $Ar_2$ and $Ar_3$ are selected from the group consisting of aromatic rings such as a benzene ring, a naphthalene ring, and substituted aromatic rings; $R_1$ and $R_3$ are each selected from the group consisting of hydrogen, a lower alkyl group, a phenyl group, and substituted lower alkyl groups and substituted phenyl group; and $R_2$ is selected from the group consisting of a lower alkyl group, a carboxyl group and ester groups of the carboxyl group.)

Specific examples of the azo pigments of the above formula are as follows:

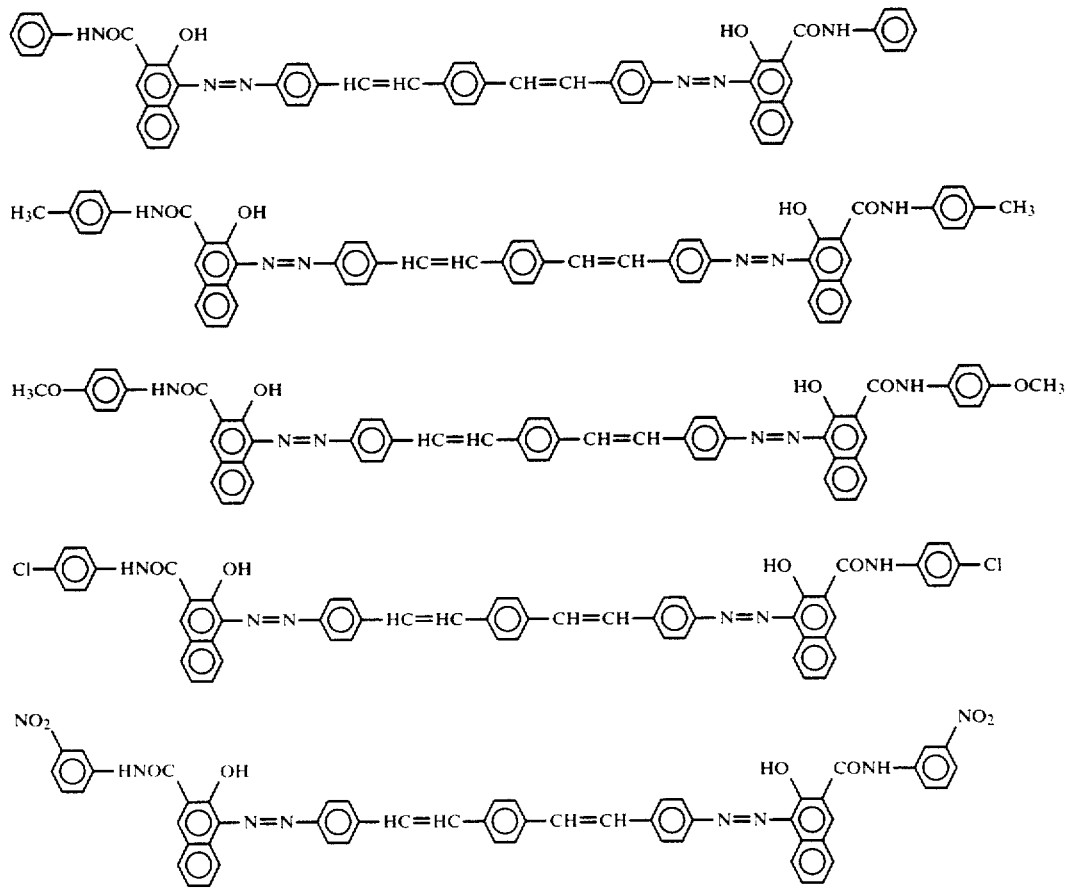

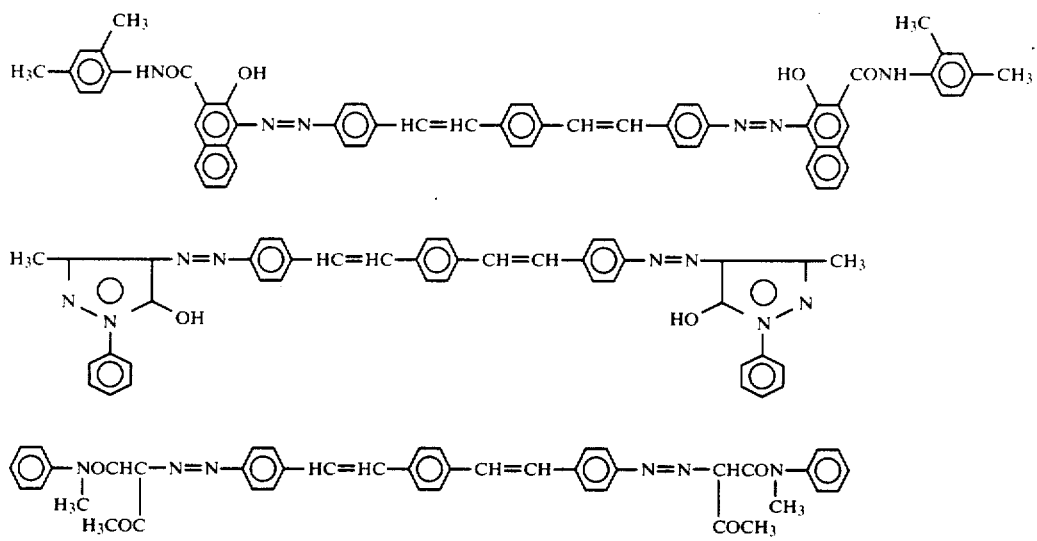
(2) Azo pigments having a triphenyoamine skeleton (Japanese Laid-Open Patent Application 53-132347)
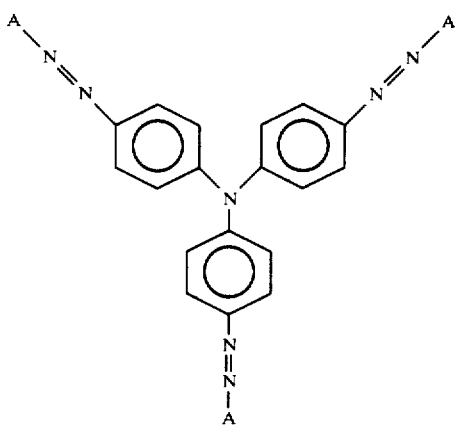
wherein A is the same as that in the formula of the above azo pigments having a distyrylbenzene skeleton disclosed in Japanese Laid-Open Patent Application 53-133445.
Specific examples of the azo pigments of the above formula are as follows:
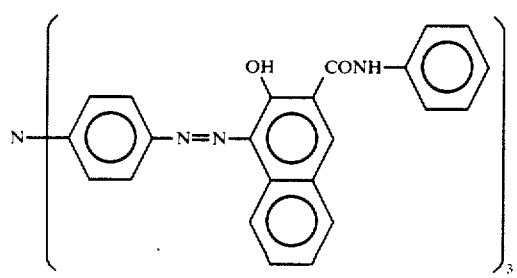
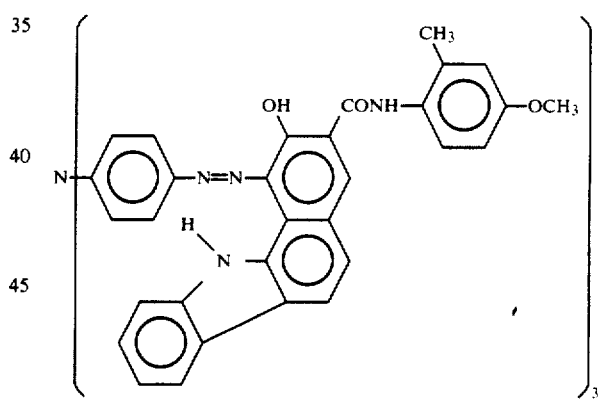
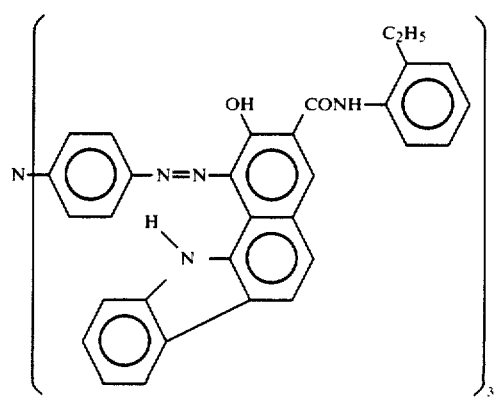

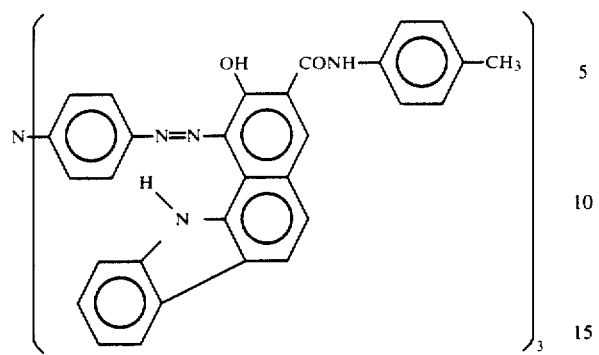
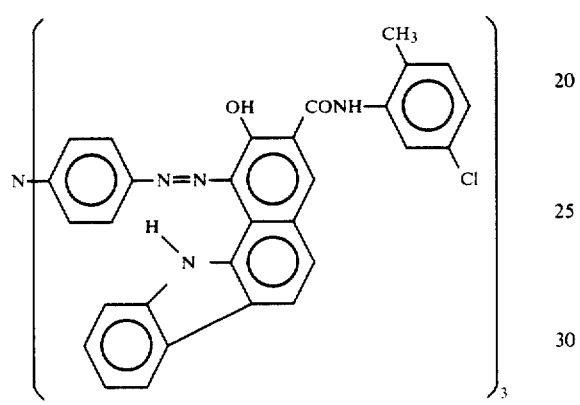
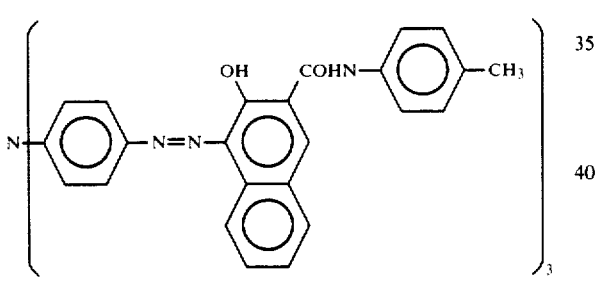
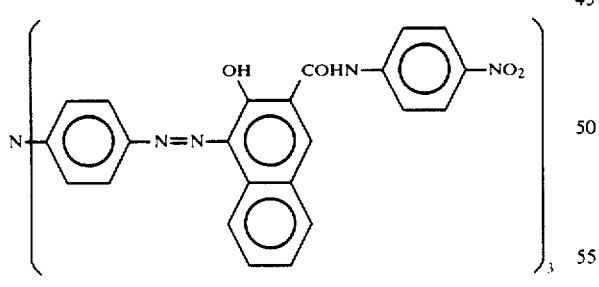
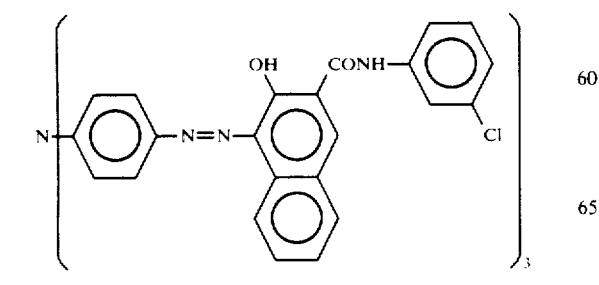
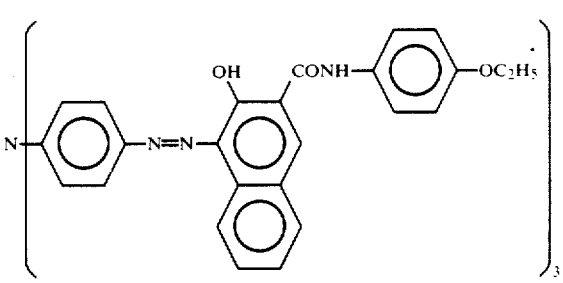
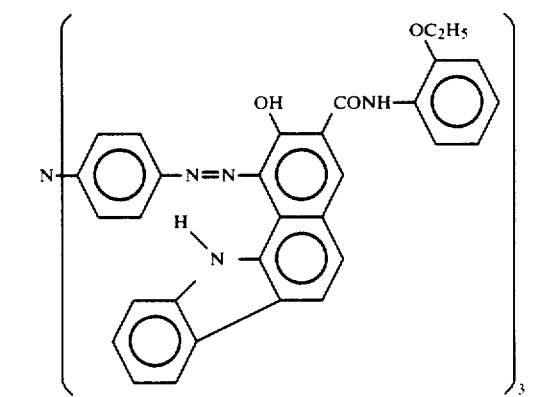
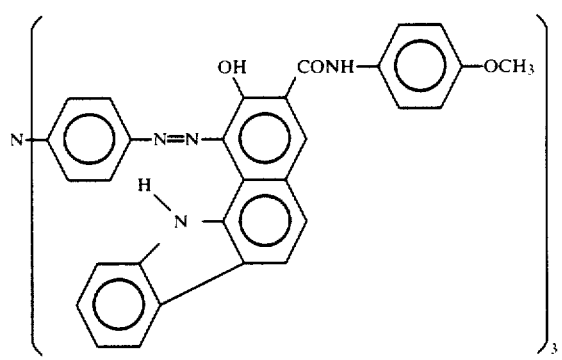
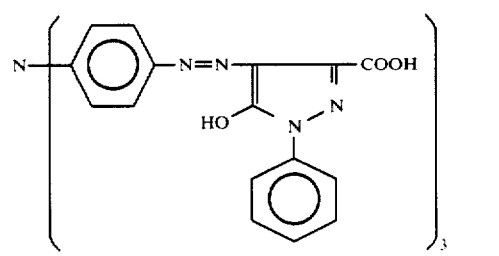
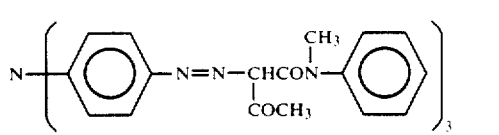
(3) Azo pigments having a fluorenone skeleton (Japanese Laid-Open Patent 54-22834)

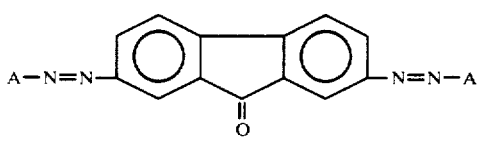

wherein A is the same as that in the formula of the azo pigments having a distyrylbenzene skeleton disclosed in Japanese Laid-Open Patent Application 53-133445.

Specific examples of the azo pigments of the above formula are as follows:

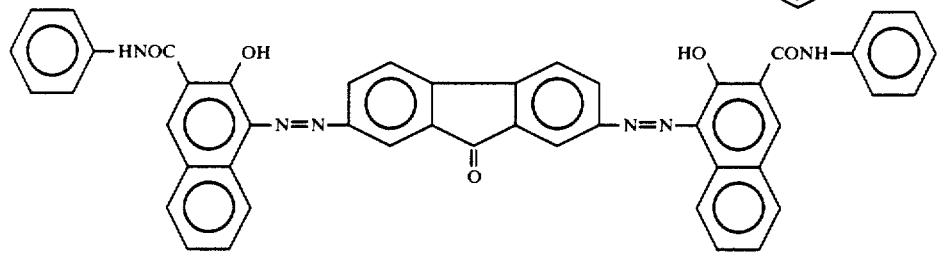

Hereinafter,

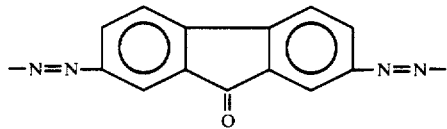

is represented by Y.

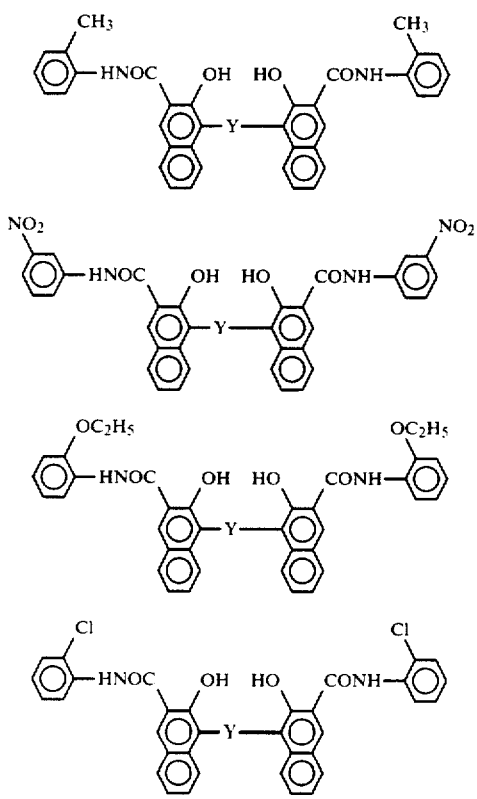

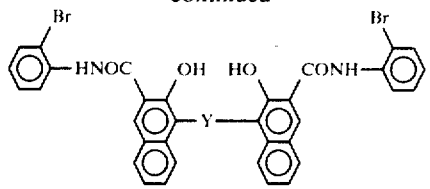

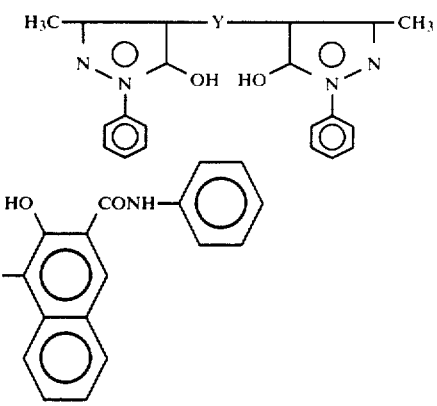

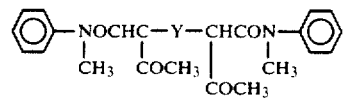

An electrophotographic photoconductor according to the present invention as shown in FIG. 3 can be prepared, for example, as follows. A charge generating material 3 is vacuum-evaporated on the electroconductive support material 1, or a charge generating material 3 in the form of fine particles is dispersed in a solution of a binder agent. This dispersion is applied to the electroconductive support material 1 and is then dried, and, if necessary, the applied layer is subjected to buffing to make the surface smooth or to adjust the thickness of the layer to a predetermined thickness, whereby a charge generating layer 5 is formed. A charge transporting layer 6 is then formed on the charge generating layer 5 by applying a solution of one or more 1,3-dithiol derivatives and a binder agent to the charge generating layer 5 and then drying. In this photoconductor, the charge generating material employed is the same as that employed in the photoconductor shown in FIG. 2.

It is preferable that the thickness of the charge generating layer 5 be less than 5 μm, more preferably less than 2 μm. It is preferable that the thickness of the charge transporting layer 6 be in the range of 3 μm to 50 μm, more preferably in the range of 5 μm to 20 μm. In the case where the charge generating layer 5 comprises a charge generating material in the form of fine particles, dispersed in a binder agent, it is preferable that the amount of the charge generating material in the charge generating layer 5 be in the range of 10 wt. % to 95 wt. % of the entire weight of the charge generating layer 5, more preferably in the range of 50 wt. % to 90 wt. %. Further, it is preferable that the amount of the styryl 1,3-dithiol derivative contained in the charge transporting layer 6 be in the range of 10 wt. % to 95 wt. %, more preferably in the range of 30 wt. % to 90 wt. % of the total weight of the charge transporting layer 6.

As the electroconductive support material 1 for use in the present invention, a metal plate or metal foil, for example, made of aluminum, a plastic film on which a metal, for example, alumimum, is evaporated, or paper which has been treated so as to be electroconductive, can be employed.

As the binder agent for use in the present invention, condensation resins, such as polyamide, polyurethane polyester, epoxy resin, polyketone and polycarbonate; and vinyl polymers such as polyvinylketone, polystyrene, poly-N-vinylcarbazole and polyacrylamide, can be used.

Other conventional electrically insulating and adhesive resins can also be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive or barrier layer can be disposed between the electroconductive support material and the photosensitive layer. The adhesive layer or the barrier layer can be made of, for example, polyamide, nitrocellulose, or aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of embodiments of an electrophotographic photoconductor according to the present invention will now be explained in detail by referring to the following examples.

EXAMPLE 1

The following components were ground and dispersed in a ball mill to prepare a charge generating layer formation liquid:

|  | Parts by Weight |
|---|---|
| Diane Blue (C.I. Pigment Blue 25, C.I. 21180) (a charge generating pigment of the following formula (CG-1)) | 76 |
| 2% tetrahydrofuran solution of a polyester resin (Vylon 200 made by Toyobo Co., Ltd.) | 1,260 |
| Tetrahydrofuran | 3,700 |

The charge generating layer formation liquid was coated by a doctor blade on the aluminum-evaporated surface of an aluminum-evaporated polyester base film, which served as an electroconductive support material, so that a charge generating layer, with a thickness of about 1 μm when dried at room temperature, was formed on the electroconductive support material.

Then the following components were mixed and dissolved, so that a charge transporting layer formation liquid was prepared:

|  | Parts by Weight |
|---|---|
| 1,3-dithiol derivative No. 2 in Table 2 | 2 |
| Polycarbonate resin (Panlite K 1300 made by Teijin Limited.) | 2 |
| Tetrahydrofuran | 16 |

The thus prepared charge transporting layer formation liquid was coated on the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 1 according to the present invention was prepared.

The electrophotographic photoconductor No. 1 was charged negatively in the dark under application of −6KV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 20 lux, and the exposure $E_{\frac{1}{2}}$ (lux. seconds) required to reduce the initial surface potential Vop (V) to ½ the initial surface potential Vpo (V) was measured. The results showed that Vpo (V)=−1321 V and $E_{\frac{1}{2}}$=2.5 lux. seconds.

EXAMPLES 2 THROUGH 4

Example 1 was repeated except that the charge generating material and the 1,3-dithiol derivative which worked as the charge transporting material employed in Example 1 were replaced by the charge generating materials and the 1,3-dithiol derivatives, respectively, as listed in Table 2, whereby electrophotographic photoconductor No. 2 through No. 4 according to the present invention were prepared.

Vpo and $E_{\frac{1}{2}}$ of those electrophotographic photoconductors were measured in the same manner as in Example 1. The results are shown in Table 3.
TABLE 2
| Example No. 2 Photoconductor No. | Charge Generating Material | Charge Transporting Material (1,3-dithiol derivative No. in Table 1) |
|---|---|---|
| 2 | 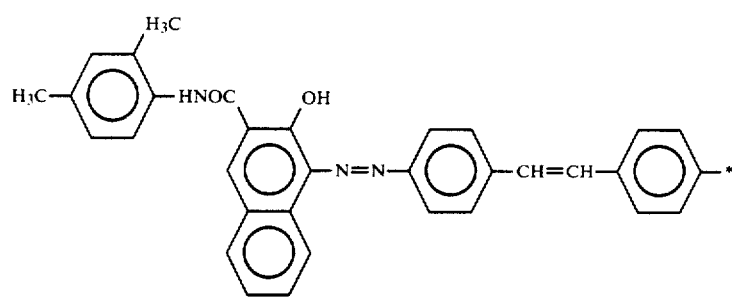 | 3 |
| | 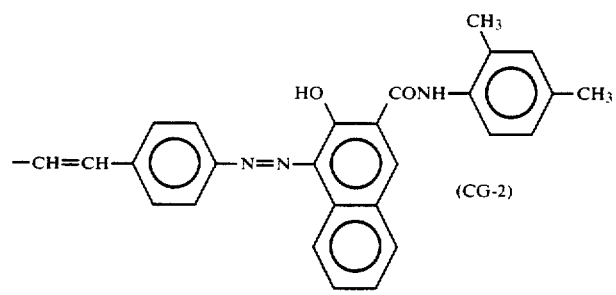 (CG-2) | |
| 3 | 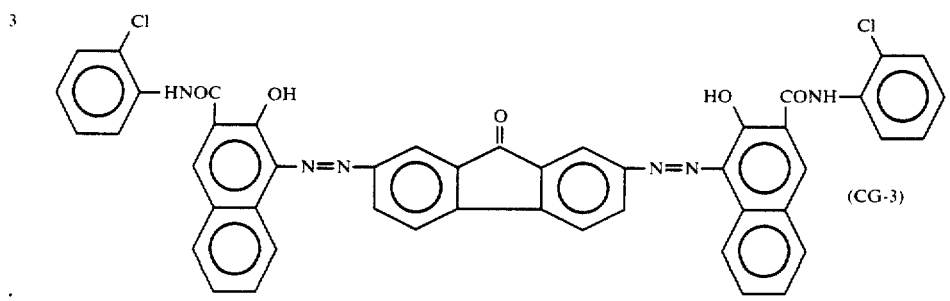 (CG-3) | 5 |

TABLE 2-continued

| Example No. 2 Photoconductor No. | Charge Generating Material | Charge Transporting Material (1,3-dithiol derivative No. in Table 1) |
|---|---|---|
| 4 | (CG-4) | 7 |

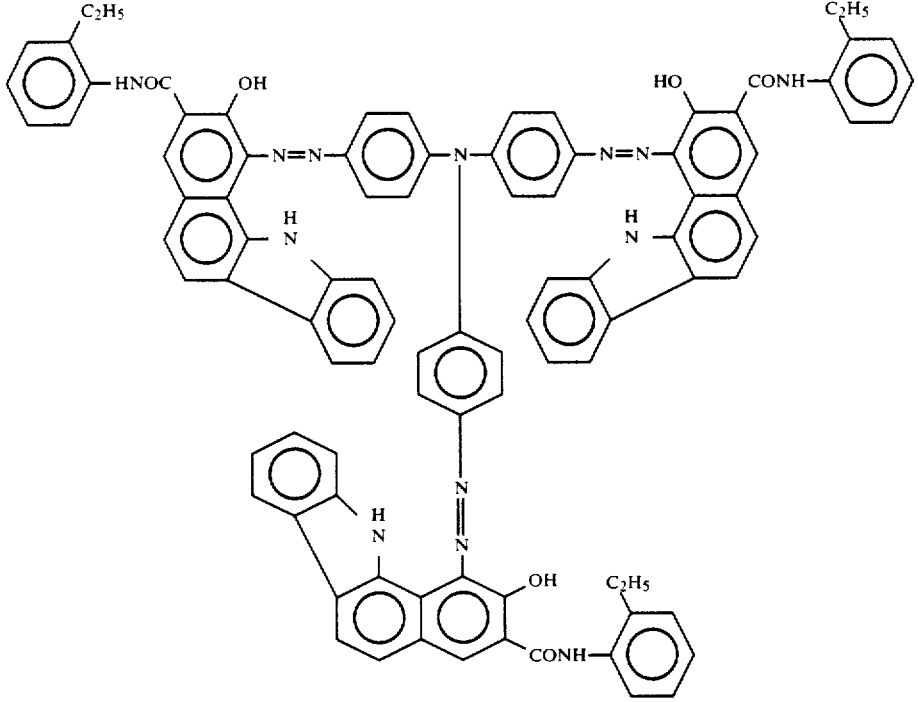

EXAMPLE 5

Selenium was vacuum-evaporated with a thickness of approximately 1.0 μm on an approximately 300 μm thick aluminum plate so that a charge generating layer was formed on the aluminum plate.

A charge transporting layer liquid was prepared by mixing and dispersing the following components:

| | Parts by Weight |
|---|---|
| 1,3-dithiol derivative No. 9 in Table 1 | 2 |
| Polyester resin (Polyester Adhesive 49000 made by Du Pont Co.) | 3 |
| Tetrahydrofuran | 45 |

The thus prepared charge transporting layer liquid was coated on the aforementioned selenium charge generating layer by a doctor blade, dried at room temperature and then dried under reduced pressure, so that a charge transporting layer about 13 μm thick was formed on the charge generating layer; thus, an electrophotographic photoconductor No. 5 according to the present invention was prepared.

Vpo and $E_{\frac{1}{2}}$ were measured. The results showed that Vpo $= -1215$ V and $E_{\frac{1}{2}} = 3.7$ lux. seconds.

EXAMPLE 6

One part by weight of Diane Blue (C.I. Pigment Blue 25, C.I. 21180) which was the same as that employed in Example 1 was added to 158 parts by weight of tetrahydrofuran, and the mixture was ground and dispersed in a ball mill. To this mixture, 12 parts by weight of the 1,3-dithiol derivative No. 12 in Table 1 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was coated on an aluminum-evaporated polyester film by a doctor blade and was dried at 100° C. for 30 minutes, so that a photosensitive layer with a thickness of about 10 μm was formed on the aluminum-evaporated polyester film, thus, an electrophotographic photoconductor No. 6 according to the present invention was prepared.

The electrophotographic photoconductor No. 6 was charged positively in the dark under application of $+6$ kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 20 lux, so that the exposure $E_{\frac{1}{2}}$ (lux seconds) required to reduce the initial surface potential Vpo (V) to $\frac{1}{2}$ the initial surface potential Vpo (V) was measured. The results showed that Vpo (V) $= +880$ V and $E_{\frac{1}{2}} = 4.0$ lux. seconds.

The charge generating material, the charge transporting material, $V_{po}$ and $E_{\frac{1}{2}}$ of each of the electrophotographic photoconductors No. 1 through No. 6 are summarized in the following Table 3:

TABLE 3

| Photo-Conductor | Charge Generating Material | Charge Transporting Material (1,3-dithiol Derivative) | $V_{po}$ (V) | $E_{\frac{1}{2}}$ (lux · seconds) |
|---|---|---|---|---|
| No. 1 | CG-1 | No. 3 | −1321 | 2.5 |
| No. 2 | CG-2 | No. 3 | −1354 | 2.2 |
| No. 3 | CG-3 | No. 5 | −1064 | 1.1 |
| No. 4 | CG-4 | No. 7 | −973 | 0.9 |
| No. 5 | Se | No. 9 | −1215 | 3.7 |
| No. 6 | CG-1 | No. 12 | +880 | 4.0 |

Each of the electrophotographic photoconductors No. 1 through No. 5 prepared in Examples 1 through 5 was negatively charged, while the electrophotographic photoconductor No. 6 prepared in Example 6 was positively charged by a commercially available copying machine, so that a latent electrostatic image was formed on each photoconductor and was developed with a dry type developer. The developed images were transferred to a high quality transfer sheet and were fixed to the transfer sheet. As a result, clear images were obtained from each of the electrophotographic photoconductors.

What is claimed is:

1. An electrophotographic photoconductor comprising an electroconductive support material and a photosensitive layer comprising at least one 1,3-dithiol derivative of the formula

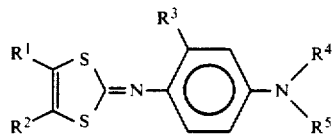

wherein $R^1$ and $R^2$ independently represent hydrogen, a substituted or unsubstituted phenyl group, or $R^1$ and $R^2$ can form a ring; $R^3$ represents hydrogen or an alkyl group; and $R^4$ and $R^5$ independently represent an alkyl group, a substituted or unsubstituted aralkyl group, or a substituted or unsubstituted aryl group.

2. An electrophotographic photoconductor as claimed in claim 1, wherein said photosensitive layer further comprises a binder agent which constitutes a charge transporting medium in combination with said 1,3-dithiol derivative; and a charge generating material dispersed within said charge transporting medium.

3. An electrophotographic photoconductor as claimed in claim 1, wherein said photosensitive layer comprises a charge generating layer containing a charge generating material, and a charge transporting layer containing said 1,3-dithiol derivative as a charge transporting material.

4. The electrophotographic photoconductor as claimed in claim 1, wherein the thickness of said photosensitive layer is in the range of 3 μm to 50 μm.

5. An electrophotographic photoconductor as claimed in claim 1, wherein the amount of said 1,3-dithiol derivative is in the range of 30 wt. % to 70 wt. % of the entire weight of said photosensitive layer.

6. An electrophotographic photoconductor as claimed in claim 2, wherein the thickness of said photosensitive layer is in the range of 3 μm to 50 μm.

7. An electrophotographic photoconductor as claimed in claim 2, wherein the amount of said 1,3-dithiol derivative is in the range of 10 wt. % to 95 wt. % of the entire weight of said photosensitive layer, and the amount of said charge generating material is in the range of 0.1 wt. % to 50 wt. % of the entire weight of said photosensitive layer.

8. An electrophotographic photoconductor as claimed in claim 3, wherein the thickness of said charge generating layer is not more than 5 μm and the thickness of said charge transporting layer is in the range of 3 μm to 50 μm.

9. An electrophotographic photoconductor as claimed in claim 3, wherein the amount of said charge generating material is in the range of 10 wt. % to 95 wt. % of the entire weight of said charge generating layer, and the amount of said 1,3-dithiol derivative is in the range of 10 wt. % to 95 wt. % of the entire weight of said charge transporting layer.

10. An electrophotographic photoconductor as claimed in claim 1 in which said 1,3-dithiol derivative is selected from the group of compounds in which the substituents $R^1$, $R^2$, $R^3$, $R^4$ and $R^5$ are as follows:

| $R^1$ | $R^2$ | $R^3$ | $R^4$ | $R^5$ |
|---|---|---|---|---|
| —C₆H₅ | H | H | —CH₃ | —CH₃ |
| —C₆H₅ | H | H | —C₂H₅ | —C₂H₅ |
| —C₆H₅ | H | —CH₃ | —C₂H₅ | —C₂H₅ |
| —C₆H₅ | H | H | —CH₂—C₆H₅ | —CH₂—C₆H₅ |
| —C₆H₅ | H | H | —C₆H₅ | —C₆H₅ |
| —C₆H₅ | H | H | —CH₂—C₆H₄—CH₃ | —CH₂—C₆H₄—CH₃ |

| R¹ | R² | R³ | R⁴ | R⁵ |
|---|---|---|---|---|
| –C₆H₅ | H | H | –CH₂–C₆H₄–OCH₃ | –CH₂–C₆H₄–OCH₃ |
| –C₆H₄–CH₃ | H | –CH₃ | –C₂H₅ | –C₂H₅ |
| –C₆H₄–OCH₃ | H | –CH₃ | –C₂H₅ | –C₂H₅ |
| –C₆H₄–OCH₃ | H | H | –C₆H₅ | –C₆H₅ |
| –C₆H₅ | –C₆H₅ | H | –CH₃ | –CH₃ |
| –C₆H₅ | –C₆H₅ | H | –CH₂–C₆H₄–CH₃ | –CH₂–C₆H₄–CH₃ |
| –CH=CH–CH=CH– | | –CH₃ | –C₂H₅ | –C₂H₅ |
| –CH=CH–CH=CH– | | H | –C₆H₅ | –C₆H₅ |
| –CH=CH–CH=CH– | | H | –CH₂–C₆H₅ | –CH₂–C₆H₅ |

* * * * *